(12) United States Patent
Biltagi

(10) Patent No.: US 11,484,672 B2
(45) Date of Patent: Nov. 1, 2022

(54) OPIOID OVERDOSE TREATMENT ASSEMBLY

(71) Applicant: Shareef J. Biltagi, Santa Ana, CA (US)

(72) Inventor: Shareef J. Biltagi, Santa Ana, CA (US)

(*) Notice: Subject to any disclaimer, the term of this patent is extended or adjusted under 35 U.S.C. 154(b) by 590 days.

(21) Appl. No.: 16/589,899

(22) Filed: Oct. 1, 2019

(65) Prior Publication Data

US 2021/0093806 A1 Apr. 1, 2021

(51) Int. Cl.
*A61M 15/00* (2006.01)
*A61B 5/00* (2006.01)

(52) U.S. Cl.
CPC ....... *A61M 15/0065* (2013.01); *A61B 5/0022* (2013.01); *A61B 5/6801* (2013.01); *A61M 15/009* (2013.01)

(58) Field of Classification Search
CPC .......... A61M 15/0009; A61M 15/0065; A61B 5/0022; A61B 5/6801
See application file for complete search history.

(56) References Cited

U.S. PATENT DOCUMENTS

| D328,244 S | 7/1992 | Hamilton |
|---|---|---|
| 9,542,826 B2 | 1/2017 | Edwards |
| 2005/0248453 A1* | 11/2005 | Fechter ............... G08B 25/016 340/539.15 |
| 2016/0361507 A1 | 12/2016 | Levin |
| 2017/0172522 A1 | 6/2017 | Insler |
| 2018/0185593 A1 | 7/2018 | Nyirucz |
| 2018/0193575 A1 | 7/2018 | Hieronymus |
| 2019/0015323 A1 | 1/2019 | Keegan |
| 2019/0374173 A1* | 12/2019 | Kiani ..................... A61B 5/747 |
| 2020/0394895 A1* | 12/2020 | Frazier .................. H04W 4/029 |

FOREIGN PATENT DOCUMENTS

| GB | 2349818 | * 4/2000 | ............... A61K 9/00 |
|---|---|---|---|
| WO | WO2014106096 | 7/2014 | |

* cited by examiner

*Primary Examiner* — Myron Wyche

(57) ABSTRACT

A opioid overdose treatment assembly for treating an opioid overdose includes a housing that can be worn on a user. An inhaler is coupled to the housing and the inhaler contains an aerosolized medication for treating an opioid overdose. The inhaler is actuatable to release a pre-determined amount of the aerosolized medication for inhalation by the user when the user is suffering from an opioid overdose. A communicator is coupled to the housing and the communicator is in wireless communication with a communication network. In this way the communicator can be placed in communication with emergency responders.

8 Claims, 5 Drawing Sheets

OPIOID OVERDOSE TREATMENT ASSEMBLY

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to overdose treatment device and more particularly pertains to a new overdose treatment device for treating an opioid overdose.

(2) Description of Related Art Including Information Disclosed Under 37 CFR 1.97 and 1.98

The prior art relates to overdose treatment device.

(h) BRIEF SUMMARY OF THE INVENTION

An embodiment of the disclosure meets the needs presented above by generally comprising a housing that can be worn on a user. An inhaler is coupled to the housing and the inhaler contains an aerosolized medication for treating an opioid overdose. The inhaler is actuatable to release a pre-determined amount of the aerosolized medication for inhalation by the user when the user is suffering from an opioid overdose. A communicator is coupled to the housing and the communicator is in wireless communication with a communication network. In this way the communicator can be placed in communication with emergency responders.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(j) DETAILED DESCRIPTION OF THE INVENTION

Figure 1:
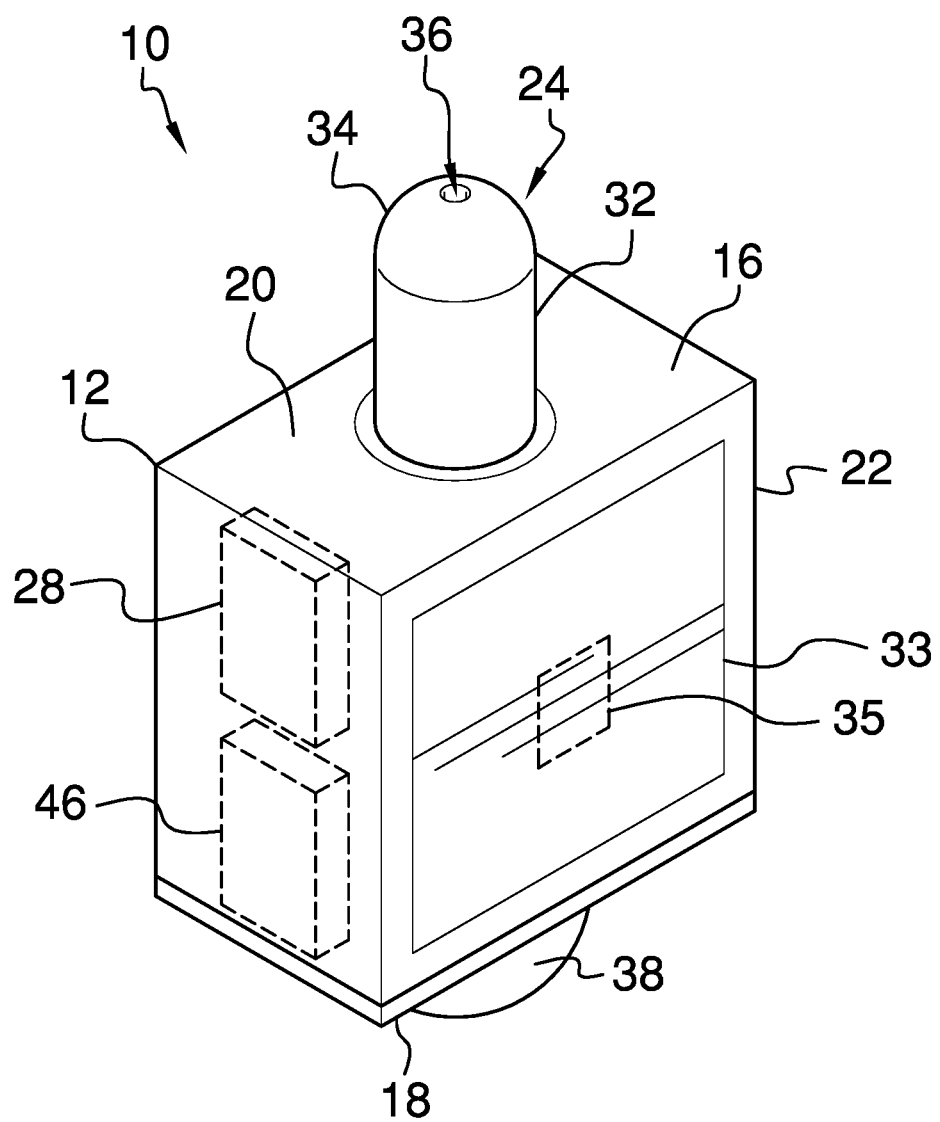
FIG. 1 is a perspective phantom view of an opioid overdose treatment assembly according to an embodiment of the disclosure.
Figure 2:
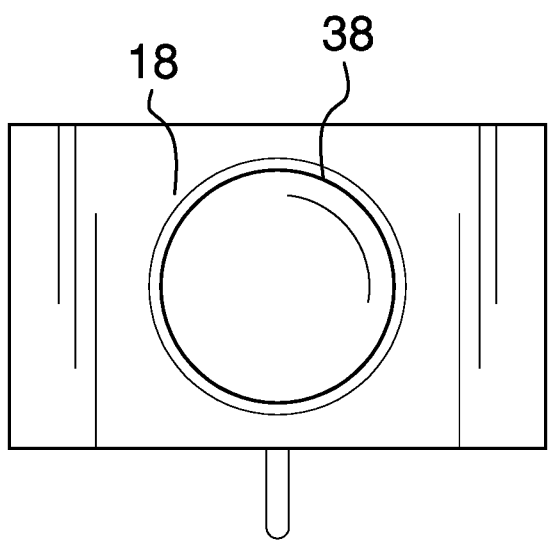
FIG. 2 is a bottom view of an embodiment of the disclosure.
Figure 3:
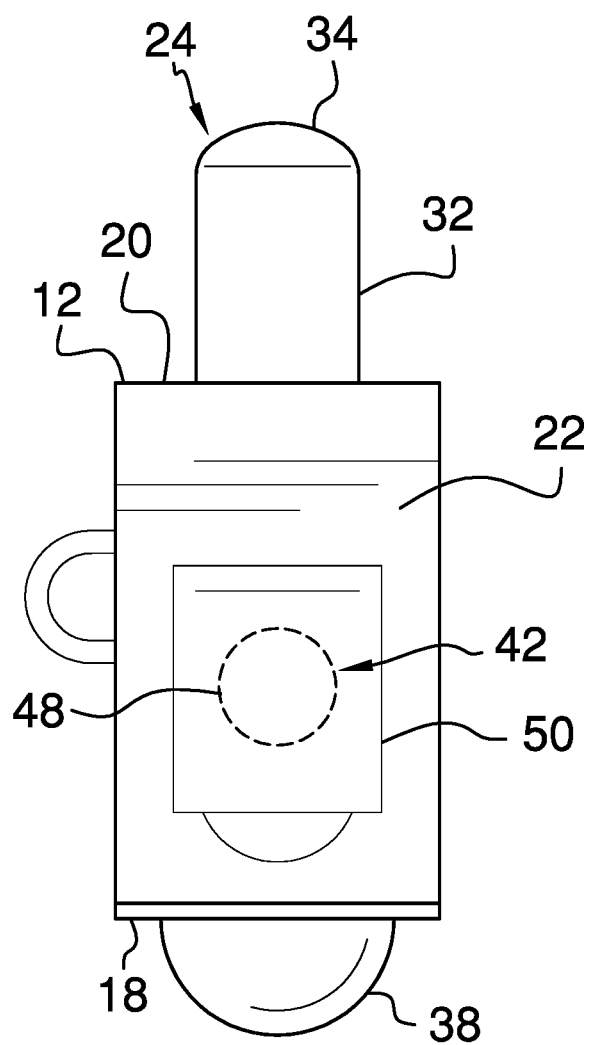
FIG. 3 is a right side phantom view of an embodiment of the disclosure.
Figure 4:
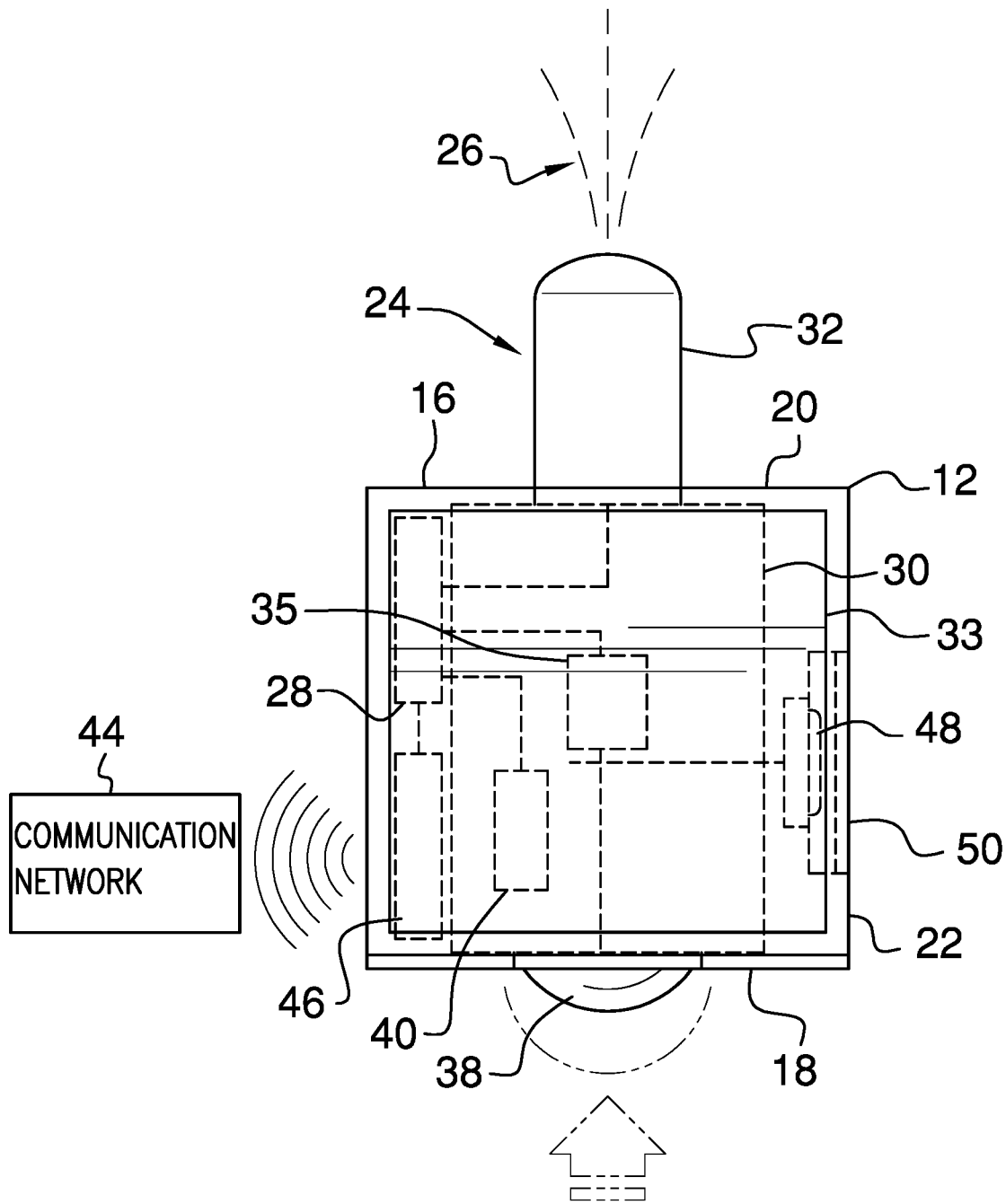
FIG. 4 is a front phantom view of an embodiment of the disclosure.
Figure 5:
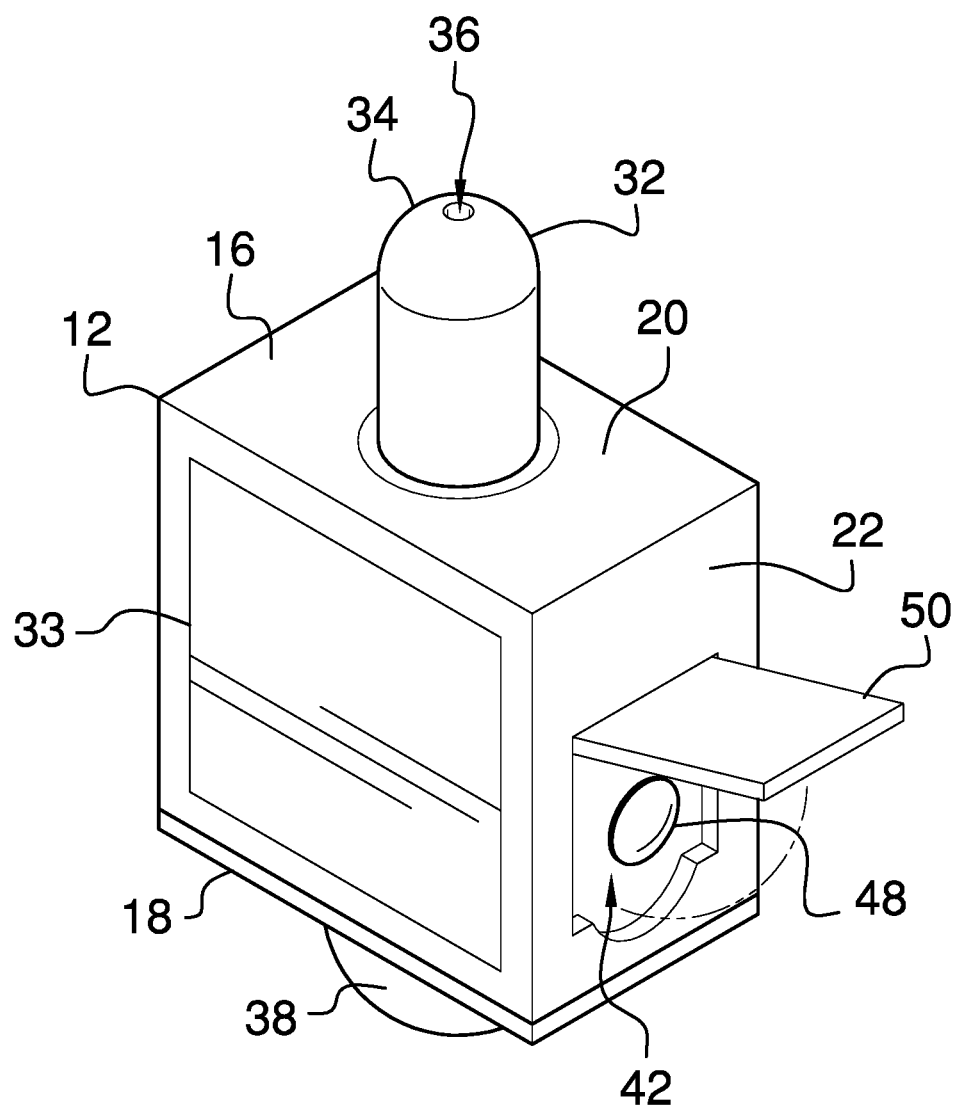
FIG. 5 is a front perspective view of an embodiment of the disclosure.
Figure 7:
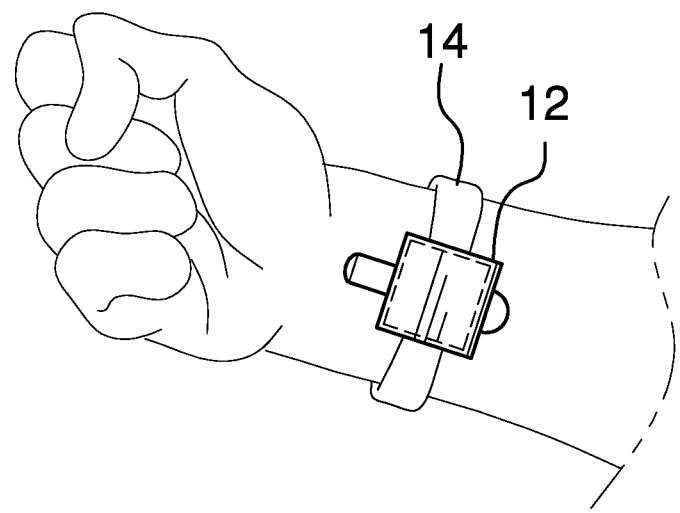
FIG. 7 is a perspective in-use view of an embodiment of the disclosure being worn as a bracelet.
Figure 6:
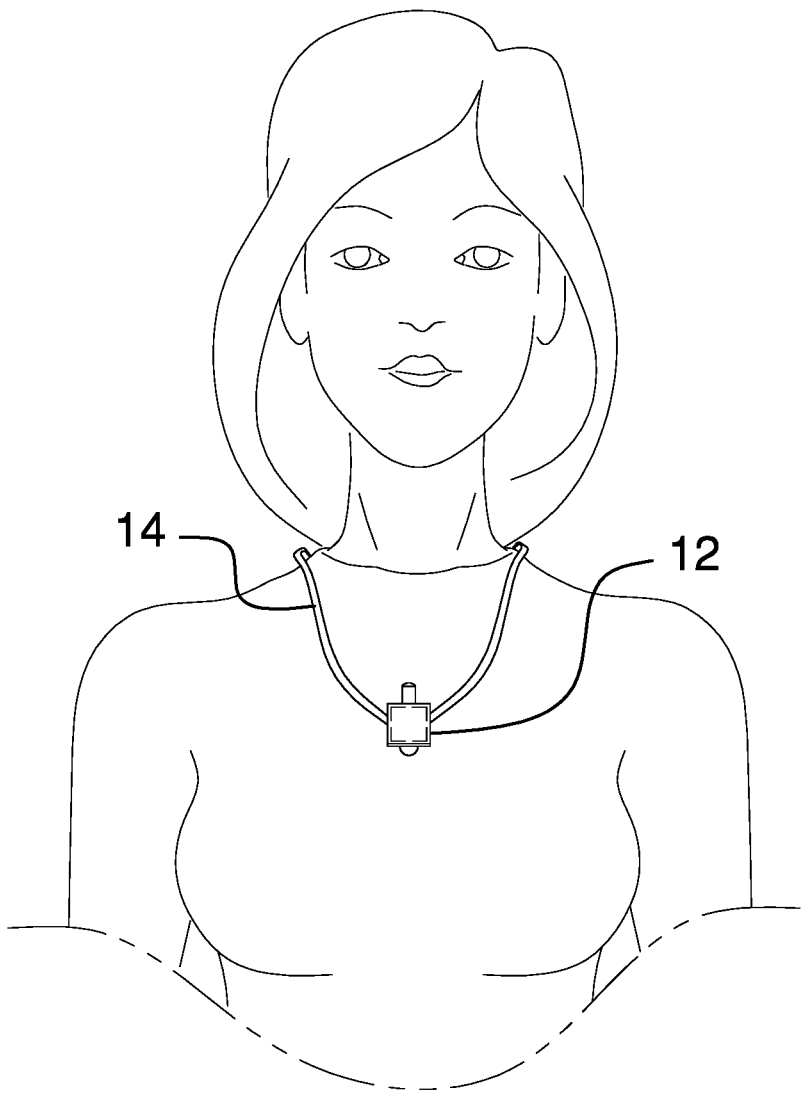
FIG. 6 is a perspective in-use view of an embodiment of the disclosure being worn as a necklace.

With reference now to the drawings, and in particular to FIGS. 1 through 7 thereof, a new overdose treatment device embodying the principles and concepts of an embodiment of the disclosure and generally designated by the reference numeral 10 will be described.

As best illustrated in FIGS. 1 through 7, the opioid overdose treatment assembly 10 generally comprises a housing 12 that is attached to a band 14 thereby facilitating the housing 12 to be worn on a user. The band 14 may comprise a bracelet for wearing around a wrist or the band 14 may comprise a necklace for wearing around a neck. The housing 12 has an outer wall 16, and the outer wall 16 has a bottom side 18, a top side 20 and a first lateral side 22. The user may be an emergency responder, an individual struggling with an opioid addiction or any other person who might associate with a person suffering from an opioid overdose.

An inhaler 24 is provided and the inhaler 24 is coupled to the housing 12. The inhaler 24 contains an aerosolized medication 26 for treating an opioid overdose. The aerosolized medication 26 may be Naloxone or other opioid antagonist used to treat opioid overdose. Moreover, the inhaler 24 is actuatable to release a pre-determined amount of the aerosolized medication 26 for inhalation by the user when the user is suffering from an opioid overdose.

The inhaler 24 comprises a control circuit 28 that is positioned in the housing 12. The control circuit 28 receives a dispense input and an alert input. A reservoir 30 is positioned within the housing 12 and the reservoir 30 contains the aerosolized medication 26. A dispenser 32 is positioned in the housing 12 and the dispenser 32 is in fluid communication with the reservoir 30. The dispenser 32 receives the pre-determined amount of the aerosolized medication 26 from the reservoir 30. The dispenser 32 extends outwardly through the top side 20 of the outer wall 16 of the housing 12 and the dispenser 32 has a distal end 34 with respect to the top side 20. The distal end 34 has an opening 36 therein for spraying the aerosolized medication 26. The dispenser 32 is actuated to spray the pre-determined amount of the aerosolized medication 26 when the control circuit 28 receives the dispense input. Additionally, the dispenser 32 may be an electronic aerosol dispenser 32 that is calibrated to release an effective dosage of opioid antagonist.

A pulse oximeter 33 is coupled to the outer wall 16 of the housing 12. Thus, the pulse oximeter 33 is in contact with skin when the user wears the housing 16. In this way the pulse oximeter 33 can sense blood oxygen levels of the user as well as the user's pulse rate. The pulse oximeter 33 is electrically coupled to the control circuit 28. Additionally, the pulse oximeter 33 may comprise an electronic pulse oximeter of any conventional design, such as infra-red pulse oximeters. A thermometer 35 is integrated into the pulse oximeter 33 such that the thermometer 35 is in thermal communication with the user's skin when the user wears the housing. In this way the thermometer 35 can monitor the user's temperature. The thermometer 35 is electrically coupled to the control circuit 28 and the thermometer 35 may comprise an electronic temperature sensor.

The inhaler 24 includes a dispense button 38 that is movably coupled to the bottom side 18 of the outer wall 16 of the housing 12. The dispense button 38 is electrically coupled to the control circuit 28. The control circuit 28 receives the dispense input when the dispense button 38 is depressed. A power supply 40 is positioned within the housing 12, the power supply 40 is electrically coupled to the control circuit 28 and the power supply 40 comprises at least one battery.

A communicator 42 is coupled to the housing 12 and the communicator 42 is in wireless communication with a communication network 44. In this way the communicator 42 is in communication with emergency responders, such as local police, local ambulance service or 911 dispatch. The communicator 42 transmits an emergency alert to the emergency responders when the communicator 42 is turned on. In this way the emergency responders are alerted that the user is suffering from the opioid overdose.

The communicator 42 comprises a transceiver 46 that is coupled to the housing 12. The transceiver 46 is electrically coupled to the control circuit 28 and the transceiver 46 is in wireless communication with the communication network 44. The communication network 44 may be the internet, a cellular phone network or any other means of wireless communication. The transceiver 46 is actuated to broadcast the emergency alert to the emergency responders when the control circuit 28 receives the alert input. The transceiver 46 may be a radio frequency transceiver 46 or the like and the transceiver 46 may employ a WPAN signal. The transceiver 46 may employ Bluetooth communication protocols such that the transceiver 46 can be paired with a personal electronic device. In this way the personal electronic device can continuously receive pulse oximetry data and temperature data from the communicator 42.

The communicator 42 includes an alert button 48 that is movably coupled to the housing 12. The alert button 48 is recessed into the first lateral side 22 of the outer wall 16 of the housing 12. Moreover, the alert button 48 is electrically coupled to the control circuit 28 and the control circuit 28 receives the alert input when the alert button 48 is depressed. Additionally, the control circuit 28 receivers the alert input when the pulse oximetry data or the temperature data below a pre-determined threshold that indicates the possibility of an opioid overdose. The control circuit 28 may monitor the pulse oximetry data and the temperature data for a period of approximately 10.0 seconds before the control circuit 28 commands the transceiver 46 to transmit the emergency alert.

The communicator 42 includes a door 50 that is hingedly coupled to the housing 12. The door 50 is positioned on the first lateral side 22 of the outer wall 16 of the housing 12. Additionally, the door 50 is normally positioned in a closed condition having the door 50 covering the alert button 48. In this way the alert button 48 is inhibited from being inadvertently depressed. The door 50 is positionable in an open condition for exposing the alert button 48.

In use, the dispenser 32 is inserted into the user's nostril and the dispense button 38 is depressed to dispense the pre-determined amount of the aerosolized medication 26. In this way the user can be immediately treated for opioid overdose. Additionally, the door 50 can be opened to allow the alert button 48 to be depressed. In this way the emergency responders can be notified that the user needs medical assistance. The housing 12 can be worn on the user's wrist or around the user's neck. Additionally, the housing 12 can be carried as standard equipment for emergency responders.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An opioid overdose treatment assembly being configured to release a pre-determined amount of a medication to a person overdosing on an opioid, said assembly comprising:

a housing being attached to a band wherein said housing is configured to be worn on a user, said housing having an outer wall, said outer wall having a bottom side, a top side and a first lateral side;

an inhaler being coupled to said housing, said inhaler containing an aerosolized medication for treating an opioid overdose, said inhaler being actuatable to release a pre-determined amount of the aerosolized medication for inhalation by the user when the user is suffering from an opioid overdose, said inhaler comprising a control circuit being positioned in said housing, said control circuit receiving a dispense input and an alert input; and a communicator being coupled to said housing, said communicator being in wireless communication with a communication network thereby facilitating said communicator to be in communication with emergency responders, said communicator transmitting an emergency alert to the emergency responders when said communicator is turned on for alerting the emergency responders that the user is suffering from the opioid overdose, wherein said communicator comprises a transceiver being coupled to said housing, said transceiver being electrically coupled to said control circuit, said transceiver being in wireless communication with the communication network, said transceiver being actuated to broadcast the emergency alert to the emergency responders when said control circuit receives said alert input, an alert button being movably coupled to said housing, said alert button being recessed into said first lateral side of said outer wall of said housing, said alert button being electrically coupled to said control circuit, said control circuit receiving said alert input when said alert button is depressed, and a door being hingedly coupled to said housing, said door being positioned on said first lateral side of said outer wall of said housing, said door being normally positioned in a closed condition having said door covering said alert button thereby inhibiting said alert button from being inadvertently depressed, said door being positionable in an open condition for exposing said alert button.

2. The assembly according to claim 1, wherein said inhaler includes a reservoir being positioned within said housing, said reservoir containing the aerosolized medication.

3. The assembly according to claim 2, wherein said inhaler includes a dispenser being positioned in said housing, said dispenser being in fluid communication with said reservoir, said dispenser receiving the pre-determined amount of the aerosolized medication from said reservoir.

4. The assembly according to claim 3, wherein said dispenser extends outwardly through said top side of said outer wall of said housing, said dispenser having a distal end with respect to said top side, said distal end having an opening thereon for spraying the aerosolized medication, said dispenser being actuated to spray the pre-determined amount of the aerosolized medication when said control circuit receives said dispense input.

5. The assembly according to claim 4, wherein said inhaler includes a dispense button being movably coupled to said bottom side of said outer wall of said housing, said dispense button being electrically coupled to said control circuit, said control circuit receiving said dispense input when said dispense button is depressed.

6. The assembly according to claim 1, further comprising a pulse oximeter being coupled to said outer wall of said housing wherein said pulse oximeter is configured to sense blood oxygen levels of the user, said pulse oximetry unit being electrically coupled to said control circuit.

7. The assembly according to claim 1, further comprising a power supply being positioned within said housing, said power supply being electrically coupled to said control circuit, said power supply comprising at least one battery.

8. An opioid overdose treatment assembly being configured to release a pre-determined amount of a medication to a person overdosing on an opioid, said assembly comprising:

a housing being attached to a band wherein said housing is configured to be worn on a user, said housing having an outer wall, said outer wall having a bottom side, a top side and a first lateral side;

an inhaler being coupled to said housing, said inhaler containing an aerosolized medication for treating an opioid overdose, said inhaler being actuatable to release a pre-determined amount of the aerosolized medication for inhalation by the user when the user is suffering from an opioid overdose, said inhaler comprising:

a control circuit being positioned in said housing, said control circuit receiving a dispense input and an alert input;

a reservoir being positioned within said housing, said reservoir containing the aerosolized medication;

a dispenser being positioned in said housing, said dispenser being in fluid communication with said reservoir, said dispenser receiving the pre-determined amount of the aerosolized medication from said reservoir, said dispenser extending outwardly through said top side of said outer wall of said housing, said dispenser having a distal end with respect to said top side, said distal end having an opening thereon for spraying the aerosolized medication, said dispenser being actuated to spray the pre-determined amount of the aerosolized medication when said control circuit receives said dispense input;

a pulse oximeter being coupled to said outer wall of said housing wherein said pulse oximeter is configured to sense blood oxygen levels of the user, said pulse oximetry unit being electrically coupled to said control circuit;

a dispense button being movably coupled to said bottom side of said outer wall of said housing, said dispense button being electrically coupled to said control circuit, said control circuit receiving said dispense input when said dispense button is depressed; and a power supply being positioned within said housing, said power supply being electrically coupled to said control circuit, said power supply comprising at least one battery; and a communicator being coupled to said housing, said communicator being in wireless communication with a communication network thereby facilitating said communicator to be in communication with emergency responders, said communicator transmitting an emergency alert to the emergency responders when said communicator is turned on for alerting the emergency responders that the user is suffering from the opioid overdose, said communicator comprising:

a transceiver being coupled to said housing, said transceiver being electrically coupled to said control circuit, said transceiver being in wireless communication with the communication network, said transceiver being actuated to broadcast the emergency alert to the emergency responders when said control circuit receives said alert input;

an alert button being movably coupled to said housing, said alert button being recessed into said first lateral side of said outer wall of said housing, said alert button being electrically coupled to said control circuit, said control circuit receiving said alert input when said alert button is depressed; and a door being hingedly coupled to said housing, said door being positioned on said first lateral side of said outer wall of said housing, said door being normally positioned in a closed condition having said door covering said alert button thereby inhibiting said alert button from being inadvertently depressed, said door being positionable in an open condition for exposing said alert button.

\* \* \* \* \*